United States Patent
Tormo I Blasco et al.

(10) Patent No.: US 7,601,673 B2
(45) Date of Patent: Oct. 13, 2009

(54) FUNGICIDAL MIXTURES

(75) Inventors: Jordi Tormo I Blasco, Laudenbach (DE); Thomas Grote, Wachenheim (DE); Maria Scherer, Godramstein (DE); Reinhard Stierl, Freinsheim (DE); Siegfried Strathmann, Limburgerhof (DE); Ulrich Schöfl, Brühl (DE); Markus Gewehr, Kastellaun (DE); Bernd Müller, Frankenthal (DE); Miguel Octavio Suarez-Cervieri, Neustadt-Hambach (DE); Matthias Niedenbrück, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 307 days.

(21) Appl. No.: 11/579,085

(22) PCT Filed: Apr. 23, 2005

(86) PCT No.: PCT/EP2005/004387

§ 371 (c)(1),
(2), (4) Date: Oct. 30, 2006

(87) PCT Pub. No.: WO2005/104847

PCT Pub. Date: Nov. 10, 2005

(65) Prior Publication Data

US 2008/0064597 A1    Mar. 13, 2008

(30) Foreign Application Priority Data

Apr. 30, 2004    (DE) ................. 10 2004 021 766
May 18, 2004    (DE) ................. 10 2004 025 032

(51) Int. Cl.
A01N 25/00    (2006.01)
A01N 59/04    (2006.01)

(52) U.S. Cl. .................................. 504/116.1; 504/101
(58) Field of Classification Search .............. 504/116.1, 504/101
See application file for complete search history.

(56) References Cited

U.S. PATENT DOCUMENTS 6,117,876 A * 9/2000 Pees et al. ............... 514/259.31
6,350,748 B1    2/2002 Takeyama et al.

FOREIGN PATENT DOCUMENTS

EP    1 031 571 A1    8/2000
JP    2001-1192381 A    1/2000
JP    2001-192381    *    7/2001
JP    2001-192381 A    7/2001
WO    WO-03/053145 A1    7/2003

OTHER PUBLICATIONS

Database WPI, Section Ch, Week 200428, Derwent Publications Ltd., London, GB; Class C02, AN 2003-586936. XP002331636.

* cited by examiner

Primary Examiner—Johann R Richter
Assistant Examiner—Kristie L Brooks
(74) Attorney, Agent, or Firm—Birch, Stewart, Kolasch & Birch, LLP

(57) ABSTRACT

Fungicidal mixtures, comprising, as active components,
1) a sulfamoyl compound of the formula I, in which the substituents are as defined below:
$R^1$ is hydrogen, halogen, cyano, alkyl, haloalkyl, alkoxy, alkylthio, alkoxycarbonyl, phenyl, benzyl, formyl or CH=NOA;
A is hydrogen, alkyl, alkylcarbonyl;
$R^2$ is hydrogen, halogen, cyano, alkyl, haloalkyl, alkoxycarbonyl;
$R^3$ is halogen, cyano, nitro, alkyl, haloalkyl, alkoxy, alkylthio, alkoxycarbonyl, formyl or CH=NOA;
n is 0, 1, 2, 3 or 4;
$R^4$ is hydrogen, halogen, cyano, alkyl or haloalkyl; and
2) at least one active compound selected from the following groups:
A) azoles; B) strobilurins; C) acylalanines; D) amine derivatives; E) anilinopyrimidines; F) dicarboximides; G) cinnamides and analogs; H) dithiocarbamates; I) heterocylic compounds; K) sulfur and copper fungicides; L) nitrophenyl derivatives; M) phenylpyrroles; N) sulfenic acid derivatives; O) other fungicides; according to the description;
in a synergistically effective amount, methods for controlling harmful fungi using mixtures of a compound I with active compounds of groups A) to O) and the use of the compounds I with active compounds of groups A) to O) for preparing such mixtures, and also compositions comprising these mixtures.

21 Claims, No Drawings

FUNGICIDAL MIXTURES

The present invention relates to fungicidal mixtures comprising, as active components, 1) a sulfamoyl compound of the formula I

I in which the substituents are as defined below:

$R^1$ is hydrogen, halogen, cyano, $C_1$-$C_4$-alkyl, $C_1$-$C_2$-haloalkyl, $C_1$-$C_4$-alkoxy, $C_1$-$C_4$-alkylthio, $C_1$-$C_4$-alkoxycarbonyl, phenyl, benzyl, formyl or CH=NOA;

A is hydrogen, $C_1$-$C_4$-alkyl, $C_1$-$C_4$-alkylcarbonyl;

$R^2$ is hydrogen, halogen, cyano, $C_1$-$C_4$-alkyl, $C_1$-$C_2$-haloalkyl, $C_1$-$C_6$-alkoxycarbonyl;

$R^3$ is halogen, cyano, nitro, $C_1$-$C_4$-alkyl, $C_1$-$C_2$-haloalkyl, $C_1$-$C_4$-alkoxy, $C_1$-$C_4$-alkylthio, $C_1$-$C_4$-alkoxycarbonyl, formyl or CH=NOA;

n is 0, 1, 2, 3 or 4;

$R^4$ is hydrogen, halogen, cyano, $C_1$-$C_4$-alkyl or $C_1$-$C_2$-haloalkyl;

and 2) at least one active compound selected from the following groups:

A) azoles, such as cyproconazole, difenoconazole, epoxiconazole, fluquinconazole, flusilazole, hexaconazole, imazalil, metconazole, myclobutanil, penconazole, prochloraz, prothioconazole, tebuconazole, triadimefon, triadimenol, triflumizole;

B) strobilurins, such as azoxystrobin, dimoxystrobin, fluoxastrobin, kresoxim-methyl, metominostrobin, orysastrobin, picoxystrobin, pyraclostrobin or trifloxystrobin;

C) acylalanines, such as benalaxyl, metalaxyl, mefenoxam, ofurace, oxadixyl;

D) amine derivatives, such as spiroxamine;

E) anilinopyrimidines, such as pyrimethanil, mepanipyrim or cyprodinil;

F) dicarboximides, such as iprodione, procymidone, vinclozolin;

G) cinnamides and analogs, such as dimethomorph, flumetover or flumorph;

H) dithiocarbamates, such as ferbam, nabam, maneb, metam, metiram, propineb, polycarbamate, thiram, ziram, zineb;

I) heterocylic compounds, such as benomyl, boscalid, carbendazim, dithianon, famoxadone, fenamidone, penthiopyrad, picobenzamid, proquinazid, quinoxyfen, thiophanate-methyl, triforine, or 5-chloro-7-(4-methylpiperidin-1-yl)-6-(2,4,6-trifluorophenyl)-[1,2,4]triazolo[1,5-a]pyrimidine of the formula II,

II

K) sulfur and copper fungicides, such as Bordeaux mixture, copper acetate, copper oxychloride, basic copper sulfate;

L) nitrophenyl derivatives, such as dinocap;

M) phenylpyrroles, such as fenpiclonil or fludioxonil;

N) sulfenic acid derivatives, such as captafol, dichlofluanid, tolylfluanid;

O) other fungicides, such as benthiavalicarb, chlorothalonil, cyflufenamid, diclofluanid, diethofencarb, ethaboxam, fenhexamid, fluazinam, iprovalicarb, metrafenone, zoxamide;

oxime ether derivatives of the formula III,

III in which

X is $C_1$-$C_4$-haloalkoxy, n is 0, 1, 2 or 3,

R is halogen, $C_1$-$C_4$-alkyl, $C_1$-$C_4$-haloalkyl, $C_1$-$C_4$-alkoxy or haloalkoxy; and compounds of the formula IV,

IV in which the variables are as defined below:

A is O or N;

B is N or a direct bond;

G is C or N;

$R^{41}$ is $C_1$-$C_4$-alkyl;

$R^{42}$ is $C_1$-$C_4$-alkoxy; and $R^{43}$ is halogen;

in a synergistically effective amount.

Moreover, the invention relates to a method for controlling harmful fungi using mixtures of a compound I with active compounds of groups A) to O) and to the use of the compounds I with the active compounds of groups A) to O) for preparing such mixtures, and also to compositions comprising such mixtures.

The sulfamoyl compounds of the formula I referred to above as component 1, their preparation and their action against harmful fungi are known from the literature (EP-A 10 31 571, JP-A 2001-192 381).

Mixtures of a sulfamoyl compound of the formula I with other active compounds are described in WO 03/053145.

The active compounds of groups A) to O) mentioned above as component 2, their preparation and their action against harmful fungi are generally known (cf.: http://www.hclrss-.demon.co.uk/index.html):

cyproconazole, 2-(4-chlorophenyl)-3-cyclopropyl-1-[1,2,4]triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

enilconazole (imazalil), 1-[2-(2,4-dichlorophenyl)-2-(2-propenyloxy)ethyl]-1H-imidazole (Fruits, 1973, Vol. 2B, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fluquinconazol, 3-(2,4-dichlorophenyl)-6-fluoro-2-[1,2,4]triazol-1-yl-3H-quinazolin-4-one (Proc. Br. Crop Prot. Conf.—Pests Dis., 5-3, 411 (1992));

flusilazole, 1-{[bis-(4-fluorophenyl)methylsilanyl]methyl}-1H-[1,2,4]triazole (Proc. Br. Crop Prot. Conf.—Pests Dis., 1, 413 (1984));

hexaconazole, (RS)-2-(2,4-dichlorophenyl)-1-(1H-1,2,4-triazol-1-yl)hexan-2-ol [CAS-RN 79983-71-4;

metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile [CAS RN 88671-89-0;

penconazole, 1-[2-(2,4-dichlorophenyl)pentyl]-1H-[1,2,4]triazole (Pesticide Manual, 12th Ed. (2000), page 712);

prochloraz, N-propyl-N-[2-(2,4,6-trichlorophenooxy)ethyl]imidazole-1-carboxamide (U.S. Pat. No. 3,991,071);

prothioconazole, 2-[2-(1-chlorocyclopropyl)-3-(2-chlorophenyl)-2-hydroxypropyl]-2,4-dihydro-[1,2,4]triazol-3-thione (WO 96/16048);

tebuconazole, 1-(4-chlorophenyl)-4,4-dimethyl-3-[1,2,4]triazol-1-ylmethylpentan-3-ol (EP-A 40 345);

triadimefon, 1-(4-chlorophenoxy)-3,3-dimethyl-1-(1H-1,2,4-triazol-1-yl)-2-butanone (BE 793897);

triadimenol, β-(4-chlorophenoxy)-α-(1,1-dimethylethyl)-1H-1,2,4-triazol-1-ethanol (DE 23 24 010);

triflumizole, (4-chloro-2-trifluoromethylphenyl)-(2-propoxy-1-[1,2,4]triazol-1-ylethylidene)amine (JP-A 79/119 462);

azoxystrobin, methyl 2-{2-[6-(2-cyano-1-vinylpenta-1,3-dienyloxy)pyrimidin-4-yloxy]phenyl}-3-methoxyacrylate (EP 382 375);

dimoxystrobin, (E)-2-(methoxyimino)-N-methyl-2-[α-(2,5-xylyloxy)-o-tolyl]acetamide (EP 477 631);

enestroburin, methyl 2-{2-[3-(4-chlorophenyl)-1-methylallylideneaminooxymethyl]-phenyl}-3-methoxyacrylate (EP 936 213);

fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime (WO 97/27189);

kresoxim-methyl, methyl (E)-methoxyimino[α-(o-tolyloxy)-o-tolyl]acetate (EP 253 213);

metominostrobin, (E)-2-(methoxyimino)-N-methyl-2-(2-phenoxyphenyl)acetamide (EP 398 692);

orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552);

picoxystrobin, methyl 3-methoxy-2-[2-(6-trifluoromethylpyridin-2-yloxymethyl)phenyl]-acrylate (EP 278 595);

pyraclostrobin, methyl N-{2-[1-(4-chlorophenyl)-1H-pyrazol-3-yloxymethyl]phenyl}(N-methoxy)carbamate (WO 96/01256);

trifloxystrobin, methyl (E)-methoxyimino-{(E)-α-[1-(α,α,α-trifluoro-m-tolyl)ethylidene-aminooxy]-o-tolyl}acetate (EP 460 575);

benalaxyl, methyl N-(phenylacetyl)-N-(2,6-xylyl)-DL-alaninate (DE 29 03 612), metalaxyl-M (mefenoxam), methyl N-(methoxyacetyl)-N-(2,6-xylyl)-DL-alaninate (GB 15 00 581);

ofurace, (RS)-α-(2-chloro-N-2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059);

spiroxamine, (8-tert-butyl-1,4-dioxaspiro[4.5]dec-2-yl)diethylamine (EP-A 281 842);

pyrimethanil, (4,6-dimethylpyrimidin-2-yl)phenylamine (DD-A 151 404);

mepanipyrim, (4-methyl-6-prop-1-ynylpyrimidin-2-yl)phenylamine (EP-A 224 339);

cyprodinil, (4-cyclopropyl-6-methylpyrimidin-2-yl)phenylamine (EP-A 310 550);

iprodione, N-isopropyl-3-(3,5-dichlorophenyl)-2,4-dioxoimidazolidine-1-carboxamide (GB13 12 536);

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-A 22 07 576);

dimethomorph, 3-(4-chlorophenyl)-3-(3,4-dimethoxyphenyl)-1-morpholin-4-ylpropenone (EP 120 321);

flumetover, 2-(3,4-dimethoxyphenyl)-N-ethyl-α,α,α-trifluoro-N-methyl-p-toluamide [AGROW No. 243, 22 (1995)];

flumorph, 3-(4-fluorophenyl)-3-(3,4-dimethoxyphenyl)-1-morpholin-4-ylpropenone (EP 860 438);

ferbam, iron(3+) dimethyldithiocarbamate (U.S. Pat. No. 1,972,961);

nabam, disodium ethylenebis(dithiocarbamate) (U.S. Pat. No. 2,317,765);

maneb, manganese ethylenebis(dithiocarbamate) (U.S. Pat. No. 2,504,404);

metam, methyldithiocarbamic acid (U.S. Pat. No. 2,791,605)

metiram, zinc ammoniate ethylenebis(dithiocarbamate) (U.S. Pat. No. 3,248,400);

propineb, zinc propylenebis(dithiocarbamate) polymer (BE 611 960);

polycarbamate, bis(dimethylcarbamodithioato-κS,κS')[μ-[[1,2-ethanediylbis[carbamodithioato-κS,κS']](2-)]]di[zinc] [CAS RN 64440-88-6];

thiram, bis(dimethylthiocarbamoyl) disulfide (DE 642 532);

ziram, dimethyldithiocarbamate [CAS RN 137-30-4];

zineb, zinc ethylenebis(dithiocarbamate) (U.S. Pat. No. 2,457,674);

benomyl, N-butyl-2-acetylaminobenzoimidazole-1-carboxamide (U.S. Pat. No. 3,631,176);

boscalid, 2-chloro-N-(4'-chlorobiphenyl-2-yl)nicotinamide (EP-A 545 099);

carbendazim, methyl (1H-benzoimidazol-2-yl)carbamate (U.S. Pat. No. 3,657,443);

dithianon, 5,10-dioxo-5,10-dihydronaphtho[2,3-b][1,4]dithiine-2,3-dicarbonitrile (GB 857 383);

famoxadone, (RS)-3-anilino-5-methyl-5-(4-phenoxyphenyl)-1,3-oxazolidine-2,4-dione [CAS RN 131807-57-3];

fenamidone, (S)-1-anilino-4-methyl-2-methylthio-4-phenylimidazolin-5-one [CAS RN 161326-34-7];

penthiopyrad, (RS)-N-[2-(1,3-dimethylbutyl)-3-thienyl]-1-methyl-3-(trifluoromethyl)-1H-pyrazole-4-carboxamide (JP 10130268);

fluopicolide (picobenzamid), 2,6-dichloro-N-(3-chloro-5-trifluoromethylpyridin-2-ylmethyl)benzamide (WO 99/42447);

proquinazid, 6-iodo-2-propoxy-3-propylquinazolin-4(3H)-one (WO 97/48684);

quinoxyfen, 5,7-dichloro-4-(4-fluorophenoxy)quinoline (U.S. Pat. No. 5,240,940);

thiophanate-methyl, 1,2-phenylenebis(iminocarbonothioyl)bis(dimethylcarbamate) (DE-A 19 30 540);

triforine, N,N'-{piperazine-1,4-diylbis[(trichloromethyl)methylene]}diformamide (DE 19 01 421);

5-chloro-7-(4-methylpiperidin-1-yl)-6-(2,4,6-trifluorophenyl)-[1,2,4]triazolo[1,5-a]pyrimidine (WO 98/46607);

Bordeaux mixture, the mixture of $CuSO_4 \times 3Cu(OH)_2 \times 3CaSO_4$ [CAS RN 8011-63-0]

copper acetate, $Cu(OCOCH_3)_2$ [CAS RN 8011-63-0];

copper oxychloride, $Cu_2Cl(OH)_3$ [CAS RN 1332-40-7];

basic copper sulfate, $CuSO_4$ [CAS RN 1344-73-6];

dinocap, the mixture of 2,6-dinitro-4-octylphenyl crotonate and 2,4-dinitro-6-octylphenyl crotonate, where "octyl" is a mixture of 1-methylheptyl, 1-ethylhexyl and 1-propylpentyl (U.S. Pat. No. 2,526,660);

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th Ed. (1995), p. 482);

captafol, N-(1,1,2,2-tetrachloroethylthio)cyclohex-4-ene-1,2-dicarboximide (Phytopathology, Vol. 52, p. 754 (1962));

dichlofluanid, N-dichlorofluoromethylthio-N',N'-dimethyl-N-phenylsulfamide (DE 11 93 498);

tolylfluanid, N-dichlorofluoromethylthio-N',N'-dimethyl-N-p-tolylsulfamide (DE 11 93498);

flubenthiavalicarb (benthiavalicarb), isopropyl {(S)-1-[(1R)-1-(6-fluorobenzothiazol-2-yl)ethylcarbamoyl]-2-methylpropyl}carbamate (JP-A 09/323 984);

chlorothalonil, 2,4,5,6-tetrachloroisophthalonitrile (U.S. Pat. No. 3,290,353);

cyflufenamid, (Z)-N-[α-(cyclopropylmethoxyimino)-2,3-difluoro-6-(trifluoromethyl)benzyl]-2-phenylacetamide (WO 96/19442);

diclofluanid, 1.1-dichloro-N-[(dimethylaminosulfonyl-1-fluoro-N-phenylmethanesulfenamide [CAS-RN 1085-98-9];

diethofencarb, isopropyl 3,4-diethoxycarbanilate (EP 78 663);

ethaboxam, N-(cyano-2-thienylmethyl)4-ethyl-2-(ethylamino)-5-thiazolecarboxamide (EP-A 639 574);

fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327);

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th Ed. (1995), p. 474);

iprovalicarb, isopropyl [(1S)-2-methyl-1-(1-p-tolylethylcarbamoyl)propyl]carbamate (EP-A 472 996);

mandipropamid, (RS)-2-(4-chlorophenyl)-N-[3-methoxy-4-(prop-2-ynyloxy)phenethyl]-2-(prop-2-ynyloxy)acetamide (cf. WO 01/87822);

metrafenone, 3'-bromo-2,3,4,6'-tetramethoxy-2',6-dimethylbenzophenone (U.S. Pat. No. 5,945,567);

zoxamide, (RS)-3,5-dichloro-N-(3-chloro-1-ethyl-1-methyl-2-oxopropyl)-p-toluamide [CAS RN 156052-68-5];

oxime ether derivatives of the formula III (WO 99/14188);

compounds of the formula IV (WO 97/48648; WO 02/094797; WO 03/14103).

It is an object of the present invention, with a view to reducing the application rates and broadening the activity spectrum of the known compounds, to provide mixtures which, at a reduced total amount of active compounds applied, have improved activity against harmful fungi.

We have accordingly found that this object is achieved by the mixtures defined at the outset. Moreover, we have found that simultaneous, that is joint or separate, application of the compound I and an active compound from groups A) to O) or successive application of the compound I and an active compound from groups A) to O) allows better control of harmful fungi than is possible with the individual compounds (synergistic mixtures).

The mixtures of a compound I and an active compound from groups A) to O) or the simultaneous, that is joint or separate, use of a compound I and an active compound from groups A) to O) are distinguished by being highly active against a wide range of phytopathogenic fungi, in particular from the classes of the Ascomycetes, Deuteromycetes, Oomycetes and Basidiomycetes. Some of them act systemically and can be used in crop protection as foliar fungicides, as fungicides for seed dressing and as soil-acting fungicides.

They are particularly important for controlling a multitude of fungi on various cultivated plants, such as bananas, cotton, vegetable species (for example cucumbers, beans and cucurbits), barley, grass, oats, coffee, potatoes, corn, fruit species, rice, rye, soya, tomatoes, grapevines, wheat, ornamental plants, sugar cane and also on a large number of seeds.

They are advantageously suitable for the control of the following phytopathogenic fungi: *Blumeria graminis* (powdery mildew) on cereals, *Erysiphe cichoracearum* and *Sphaerotheca fuliginea* on cucurbits, *Podosphaera leucotricha* on apples, *Uncinula necator* on grapevines, *Puccinia* species on cereals, *Rhizoctonia* species on cotton, rice and lawns, *Ustilago* species on cereals and sugar cane, *Venturia inaequalis* on apples, *Bipolaris* and *Drechslera* species on cereals, rice and lawns, *Septoria* species on wheat, *Botrytis cinerea* on strawberries, vegetables, ornamental plants and grapevines, *Mycosphaerella* species on bananas, peanuts and cereals, *Pseudocercosporella herpotrichoides* on wheat and barley, *Pyricularia oryzae* on rice, *Phakopsora* species on soybeans, *Phytophthora infestans* on potatoes and tomatoes, *Pseudoperonospora* species on cucurbits and hops, *Plasmopara viticola* on grapevines, *Alternaria* species on fruit and vegetables and also *Fusarium* and *Verticillium* species.

They are particularly suitable for controlling harmful fungi from the class of the Oomycetes.

The compounds I and the active compounds from groups A) to O) can be applied simultaneously, that is jointly or separately, or in succession, the sequence, in the case of separate application, generally not having any effect on the result of the control measures.

In the definitions of the symbols given in the formulae I to IV, collective terms were used which are generally representative for the following substituents:

halogen: fluorine, chlorine, bromine and iodine;

alkyl: saturated straight-chain or branched hydrocarbon radicals having 1 to 4 carbon atoms, for example $C_1$-$C_4$-alkyl, such as methyl, ethyl, propyl, 1-methylethyl, butyl, 1-methylpropyl, 2-methylpropyl, 1,1-dimethylethyl;

haloalkyl: straight-chain or branched alkyl groups having 1 or 2 carbon atoms (as mentioned above), where some or all of the hydrogen atoms in these groups may be replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

The formula I represents in particular compounds in which the index n is 0, 1 or 2, preferably 0 or 1.

In addition, preference is also given to compounds I in which $R^1$ is hydrogen, methyl, ethyl, n-, or isopropyl, fluorine, chlorine, bromine, iodine, methylthio, ethylthio, trifluoromethyl, pentafluoroethyl, cyano, phenyl or formyl, especially hydrogen, bromine or methyl, in particular methyl.

Preference is likewise given to compounds I in which $R^2$ is hydrogen, fluorine, chlorine, bromine, iodine, methyl, trifluoromethyl, methoxycarbonyl, ethoxycarbonyl, n-propoxycarbonyl, isopropoxycarbonyl or n-butoxycarbonyl, especially chlorine, bromine, methoxycarbonyl, n-propoxycarbonyl or n-butoxycarbonyl, in particular bromine.

The group $R^3$ is preferably located in the 5- and/or 6-position(s). These compounds are particularly suitable for use in the mixtures according to the invention.

Preference is furthermore given to compounds I in which $R^3$ is fluorine, chlorine, bromine, iodine, cyano, nitro, methyl, ethyl, methoxy, trifluoromethyl, especially fluorine, chlorine, bromine, cyano, methyl, trifluoromethyl or methoxy, in particular fluorine.

In particular with a view to their use in the mixtures according to the invention, preference is given to the compounds II compiled in the tables below.

I

Table 1

Compounds of the formula I in which n is zero and $R^4$ is hydrogen and the combination of $R^1$ and $R^2$ for a compound corresponds in each case to one row of table I Table 2

Compounds of the formula I in which n is zero and $R^4$ is fluorine and the combination of $R^1$ and $R^2$ for a compound corresponds in each case to one row of table I Table 3

Compounds of the formula I in which n is zero and $R^4$ is chlorine and the combination of $R^1$ and $R^2$ for a compound corresponds in each case to one row of table I Table 4

Compounds of the formula I in which n is zero and $R^4$ is methyl and the combination of $R^1$ and $R^2$ for a compound corresponds in each case to one row of table I Table 5

Compounds of the formula I in which n is 1, $R^3$ is 4-fluoro and $R^4$ is hydrogen and the combination of $R^1$ and $R^2$ for a compound corresponds in each case to one row of table I Table 6

Compounds of the formula I in which n is 1, $R^3$ is 5-fluoro and $R^4$ is hydrogen and the combination of $R^1$ and $R^2$ for a compound corresponds in each case to one row of table I Table 7

Compounds of the formula I in which n is 1, $R^3$ is 6-fluoro and $R^4$ is hydrogen and the combination of $R^1$ and $R^2$ for a compound corresponds in each case to one row of table I Table 8

Compounds of the formula I in which n is 1, $R^3$ is 7-fluoro and $R^4$ is hydrogen, and the combination of $R^1$ and $R^2$ for a compound corresponds in each case to one row of table I Table 9

Compounds of the formula I in which n is 1, $R^3$ is 4-chloro and $R^4$ is hydrogen and the combination of $R^1$ and $R^2$ for a compound corresponds in each case to one row of table I Table 10

Compounds of the formula I in which n is 1, $R^3$ is 5-chloro and $R^4$ is hydrogen and the combination of $R^1$ and $R^2$ for a compound corresponds in each case to one row of table I Table 11

Compounds of the formula I in which n is 1, $R^3$ is 6-chloro and $R^4$ is hydrogen and the combination of $R^1$ and $R^2$ for a compound corresponds in each case to one row of table I Table 12

Compounds of the formula I in which n is 1, $R^3$ is 7-chloro and $R^4$ is hydrogen and the combination of $R^1$ and $R^2$ for a compound corresponds in each case to one row of table I Table 13

Compounds of the formula I in which n is 1, $R^3$ is 4-bromo and $R^4$ is hydrogen and the combination of $R^1$ and $R^2$ for a compound corresponds in each case to one row of table I Table 14

Compounds of the formula I in which n is 1, $R^3$ is 5-bromo and $R^4$ is hydrogen, and the combination of $R^1$ and $R^2$ for a compound corresponds in each case to one row of table I Table 15

Compounds of the formula I in which n is 1, $R^3$ is 6-bromo and $R^4$ is hydrogen and the combination of $R^1$ and $R^2$ for a compound corresponds in each case to one row of table I Table 16

Compounds of the formula I in which n is 1, $R^3$ is 7-bromo and $R^4$ is hydrogen and the combination of $R^1$ and $R^2$ for a compound corresponds in each case to one row of table I Table 17

Compounds of the formula I in which n is 1, $R^3$ is 4-iodo and $R^4$ is hydrogen and the combination of $R^1$ and $R^2$ for a compound corresponds in each case to one row of table I Table 18

Compounds of the formula I in which n is 1, $R^3$ is 5-iodo and $R^4$ is hydrogen and the combination of $R^1$ and $R^2$ for a compound corresponds in each case to one row of table I Table 19

Compounds of the formula I in which n is 1, $R^3$ is 6-iodo and $R^4$ is hydrogen, and the combination of $R^1$ and $R^2$ for a compound corresponds in each case to one row of table I Table 20

Compounds of the formula I in which n is 1, $R^3$ is 7-iodo and $R^4$ is hydrogen, and the combination of $R^1$ and $R^2$ for a compound corresponds in each case to one row of table I Table 21

Compounds of the formula I in which n is 1, $R^3$ is 4-methyl and $R^4$ is hydrogen, and the combination of $R^1$ and $R^2$ for a compound corresponds in each case to one row of table I Table 22

Compounds of the formula I in which n is 1, $R^3$ is 5-methyl and $R^4$ is hydrogen, and the combination of $R^1$ and $R^2$ for a compound corresponds in each case to one row of table I Table 23

Compounds of the formula I in which n is 1, $R^3$ is 6-methyl and $R^4$ is hydrogen, and the combination of $R^1$ and $R^2$ for a compound corresponds in each case to one row of table I Table 24

Compounds of the formula I in which n is 1, $R^3$ is 7-methyl and $R^4$ is hydrogen, and the combination of $R^1$ and $R^2$ for a compound corresponds in each case to one row of table I Table 25

Compounds of the formula I in which n is 1, $R^3$ is 4-ethyl and $R^4$ is hydrogen, and the combination of $R^1$ and $R^2$ for a compound corresponds in each case to one row of table I Table 26

Compounds of the formula I in which n is 1, $R^3$ is 5-ethyl and $R^4$ is hydrogen, and the combination of $R^1$ and $R^2$ for a compound corresponds in each case to one row of table I Table 27

Compounds of the formula I in which n is 1, $R^3$ is 6-ethyl and $R^4$ is hydrogen, and the combination of $R^1$ and $R^2$ for a compound corresponds in each case to one row of table I Table 28

Compounds of the formula I in which n is 1, $R^3$ is 7-ethyl and $R^4$ is hydrogen, and the combination of $R^1$ and $R^2$ for a compound corresponds in each case to one row of table I Table 29

Compounds of the formula I in which n is 1, $R^3$ is 4-methoxy and $R^4$ is hydrogen, and the combination of $R^1$ and $R^2$ for a compound corresponds in each case to one row of table I Table 30

Compounds of the formula I in which n is 1, $R^3$ is 5-methoxy and $R^4$ is hydrogen, and the combination of $R^1$ and $R^2$ for a compound corresponds in each case to one row of table I Table 31

Compounds of the formula I in which n is 1, $R^3$ is 6-methoxy and $R^4$ is hydrogen, and the combination of $R^1$ and $R^2$ for a compound corresponds in each case to one row of table I Table 32

Compounds of the formula I in which n is 1, $R^3$ is 7-methoxy and $R^4$ is hydrogen, and the combination of $R^1$ and $R^2$ for a compound corresponds in each case to one row of table I Table 33

Compounds of the formula I in which n is 1, $R^3$ is 4-nitro and $R^4$ is hydrogen, and the combination of $R^1$ and $R^2$ for a compound corresponds in each case to one row of table I Table 34

Compounds of the formula I in which n is 1, $R^3$ is 5-nitro and $R^4$ is hydrogen, and the combination of $R^1$ and $R^2$ for a compound corresponds in each case to one row of table I Table 35

Compounds of the formula I in which n is 1, $R^3$ is 6-nitro and $R^4$ is hydrogen, and the combination of $R^1$ and $R^2$ for a compound corresponds in each case to one row of table I Table 36

Compounds of the formula I in which n is 1, $R^3$ is 7-nitro and $R^4$ is hydrogen, and the combination of $R^1$ and $R^2$ for a compound corresponds in each case to one row of table I Table 37

Compounds of the formula I in which n is 1, $R^3$ is 4-cyano and $R^4$ is hydrogen, and the combination of $R^1$ and $R^2$ for a compound corresponds in each case to one row of table I Table 38

Compounds of the formula I in which n is 1, $R^3$ is 5-cyano and $R^4$ is hydrogen, and the combination of $R^1$ and $R^2$ for a compound corresponds in each case to one row of table I Table 39

Compounds of the formula I in which n is 1, $R^3$ is 6-cyano and $R^4$ is hydrogen, and the combination of $R^1$ and $R^2$ for a compound corresponds in each case to one row of table I Table 40

Compounds of the formula I in which n is 1, $R^3$ is 7-cyano and $R^4$ is hydrogen, and the combination of $R^1$ and $R^2$ for a compound corresponds in each case to one row of table I Table 41

Compounds of the formula I in which n is 1, $R^3$ is 4-trifluoromethyl and $R^4$ is hydrogen, and the combination of $R^1$ and $R^2$ for a compound corresponds in each case to one row of table I Table 42

Compounds of the formula I in which n is 1, $R^3$ is 5-trifluoromethyl and $R^4$ is hydrogen, and the combination of $R^1$ and $R^2$ for a compound corresponds in each case to one row of table I Table 43

Compounds of the formula I in which n is 1, $R^3$ is 6-trifluoromethyl and $R^4$ is hydrogen, and the combination of $R^1$ and $R^2$ for a compound corresponds in each case to one row of table I Table 44

Compounds of the formula I in which n is 1, $R^3$ is 7-trifluoromethyl and $R^4$ is hydrogen, and the combination of $R^1$ and $R^2$ for a compound corresponds in each case to one row of table I Table 45

Compounds of the formula I in which n is 1, $R^3$ is 4-methoxycarbonyl and $R^4$ is hydrogen, and the combination of $R^1$ and $R^2$ for a compound corresponds in each case to one row of table I Table 46

Compounds of the formula I in which n is 1, $R^3$ is 5-methoxycarbonyl and $R^4$ is hydrogen, and the combination of $R^1$ and $R^2$ for a compound corresponds in each case to one row of table I Table 47

Compounds of the formula I in which n is 1, $R^3$ is 6-methoxycarbonyl and $R^4$ is hydrogen, and the combination of $R^1$ and $R^2$ for a compound corresponds in each case to one row of table I Table 48

Compounds of the formula I in which n is 1, $R^3$ is 7-methoxycarbonyl and $R^4$ is hydrogen, and the combination of $R^1$ and $R^2$ for a compound corresponds in each case to one row of table I Table 49

Compounds of the formula I in which n is 2, $R^3$ is 5,6-difluoro and $R^4$ is hydrogen, and the combination of $R^1$ and $R^2$ for a compound corresponds in each case to one row of table I Table 50

Compounds of the formula I in which n is 2, $R^3$ is 5,6-dichloro and $R^4$ is hydrogen, and the combination of $R^1$ and $R^2$ for a compound corresponds in each case to one row of table I Table 51

Compounds of the formula I in which n is 2, $R^3$ is 5,6-dibromo and $R^4$ is hydrogen, and the combination of $R^1$ and $R^2$ for a compound corresponds in each case to one row of table I Table 52

Compounds of the formula I in which n is 2, $R^3$ is 5,6-difluoro and $R^4$ is fluorine, and the combination of $R^1$ and $R^2$ for a compound corresponds in each case to one row of table I Table 53

Compounds of the formula I in which n is 2, $R^3$ is 5,6-dichloro and $R^4$ is fluorine, and the combination of $R^1$ and $R^2$ for a compound corresponds in each case to one row of table I Table 54

Compounds of the formula I in which n is 2, $R^3$ is 5,6-dibromo and $R^4$ is fluorine, and the combination of $R^1$ and $R^2$ for a compound corresponds in each case to one row of table I Table 55

Compounds of the formula I in which n is 2, $R^3$ is 5,6-difluoro and $R^4$ is chlorine, and the combination of $R^1$ and $R^2$ for a compound corresponds in each case to one row of table I Table 56

Compounds of the formula I in which n is 2, $R^3$ is 5,6-dichloro and $R^4$ is chlorine, and the combination of $R^1$ and $R^2$ for a compound corresponds in each case to one row of table I Table 57

Compounds of the formula I in which n is 2, $R^3$ is 5,6-dibromo and $R^4$ is chlorine, and the combination of $R^1$ and $R^2$ for a compound corresponds in each case to one row of table I Table 58

Compounds of the formula I in which n is 2, $R^3$ is 5,6-difluoro and $R^4$ is methyl, and the combination of $R^1$ and $R^2$ for a compound corresponds in each case to one row of table I Table 59

Compounds of the formula I in which n is 2, $R^3$ is 5,6-dichloro and $R^4$ is methyl, and the combination of $R^1$ and $R^2$ for a compound corresponds in each case to one row of table I Table 60

Compounds of the formula I in which n is 2, $R^3$ is 5,6-dibromo and $R^4$ is methyl, and the combination of $R^1$ and $R^2$ for a compound corresponds in each case to one row of table I

TABLE I

| No. | $R^1$ | $R^2$ |
|---|---|---|
| I-1 | H | H |
| I-2 | $CH_3$ | H |
| I-3 | $CH_2CH_3$ | H |
| I-4 | $CH_2CH_2CH_3$ | H |
| I-5 | F | H |
| I-6 | Cl | H |
| I-7 | Br | H |
| I-8 | I | H |
| I-9 | $SCH_3$ | H |
| I-10 | $SCH_2CH_3$ | H |
| I-11 | $CF_3$ | H |
| I-12 | $CF_2CF_3$ | H |
| I-13 | CN | H |
| I-14 | CHO | H |
| I-15 | $COOCH_3$ | H |
| I-16 | $COOCH_2CH_3$ | H |
| I-17 | $C_6H_5$ | H |
| I-18 | CH=NOH | H |
| I-19 | $CH=NOCH_3$ | H |
| I-20 | $CH=NOC(=O)CH_3$ | H |
| I-21 | H | Cl |
| I-22 | $CH_3$ | Cl |
| I-23 | $CH_2CH_3$ | Cl |
| I-24 | $CH_2CH_2CH_3$ | Cl |
| I-25 | F | Cl |
| I-26 | Cl | Cl |
| I-27 | Br | Cl |
| I-28 | I | Cl |
| I-29 | $SCH_3$ | Cl |
| I-30 | $SCH_2CH_3$ | Cl |
| I-31 | $CF_3$ | Cl |
| I-32 | $CF_2CF_3$ | Cl |
| I-33 | CN | Cl |
| I-34 | CHO | Cl |
| I-35 | $COOCH_3$ | Cl |
| I-36 | $COOCH_2CH_3$ | Cl |
| I-37 | $C_6H_5$ | Cl |
| I-38 | CH=NOH | Cl |
| I-39 | $CH=NOCH_3$ | Cl |
| I-40 | $CH=NOC(=O)CH_3$ | Cl |
| I-41 | H | F |
| I-42 | $CH_3$ | F |
| I-43 | $CH_2CH_3$ | F |
| I-44 | $CH_2CH_2CH_3$ | F |
| I-45 | F | F |
| I-46 | Cl | F |
| I-47 | Br | F |
| I-48 | I | F |
| I-49 | $SCH_3$ | F |
| I-50 | $SCH_2CH_3$ | F |
| I-51 | $CF_3$ | F |
| I-52 | $CF_2CF_3$ | F |
| I-53 | CN | F |
| I-54 | CHO | F |
| I-55 | $COOCH_3$ | F |
| I-56 | $COOCH_2CH_3$ | F |
| I-57 | $C_6H_5$ | F |
| I-58 | CH=NOH | F |
| I-59 | $CH=NOCH_3$ | F |
| I-60 | $CH=NOC(=O)CH_3$ | F |
| I-61 | H | Br |
| I-62 | $CH_3$ | Br |
| I-63 | $CH_2CH_3$ | Br |
| I-64 | $CH_2CH_2CH_3$ | Br |
| I-65 | F | Br |
| I-66 | Cl | Br |
| I-67 | Br | Br |
| I-68 | I | Br |
| I-69 | $SCH_3$ | Br |
| I-70 | $SCH_2CH_3$ | Br |
| I-71 | $CF_3$ | Br |
| I-72 | $CF_2CF_3$ | Br |
| I-73 | CN | Br |
| I-74 | CHO | Br |
| I-75 | $COOCH_3$ | Br |
| I-76 | $COOCH_2CH_3$ | Br |
| I-77 | $C_6H_5$ | Br |
| I-78 | CH=NOH | Br |
| I-79 | $CH=NOCH_3$ | Br |
| I-80 | $CH=NOC(=O)CH_3$ | Br |
| I-81 | H | I |
| I-82 | $CH_3$ | I |
| I-83 | $CH_2CH_3$ | I |
| I-84 | $CH_2CH_2CH_3$ | I |
| I-85 | F | I |

TABLE I-continued

| No. | $R^1$ | $R^2$ |
|---|---|---|
| I-86 | Cl | I |
| I-87 | Br | I |
| I-88 | I | I |
| I-89 | $SCH_3$ | I |
| I-90 | $SCH_2CH_3$ | I |
| I-91 | $CF_3$ | I |
| I-92 | $CF_2CF_3$ | I |
| I-93 | CN | I |
| I-94 | CHO | I |
| I-95 | $COOCH_3$ | I |
| I-96 | $COOCH_2CH_3$ | I |
| I-97 | $C_6H_5$ | I |
| I-98 | CH=NOH | I |
| I-99 | CH=$NOCH_3$ | I |
| I-100 | CH=NOC(=O)$CH_3$ | I |
| I-101 | H | $CH_3$ |
| I-102 | $CH_3$ | $CH_3$ |
| I-103 | $CH_2CH_3$ | $CH_3$ |
| I-104 | $CH_2CH_2CH_3$ | $CH_3$ |
| I-105 | F | $CH_3$ |
| I-106 | Cl | $CH_3$ |
| I-107 | Br | $CH_3$ |
| I-108 | I | $CH_3$ |
| I-109 | $SCH_3$ | $CH_3$ |
| I-110 | $SCH_2CH_3$ | $CH_3$ |
| I-111 | $CF_3$ | $CH_3$ |
| I-112 | $CF_2CF_3$ | $CH_3$ |
| I-113 | CN | $CH_3$ |
| I-114 | CHO | $CH_3$ |
| I-115 | $COOCH_3$ | $CH_3$ |
| I-116 | $COOCH_2CH_3$ | $CH_3$ |
| I-117 | $C_6H_5$ | $CH_3$ |
| I-118 | CH=NOH | $CH_3$ |
| I-119 | CH=$NOCH_3$ | $CH_3$ |
| I-120 | CH=NOC(=O)$CH_3$ | $CH_3$ |
| I-121 | H | $CF_3$ |
| I-122 | $CH_3$ | $CF_3$ |
| I-123 | $CH_2CH_3$ | $CF_3$ |
| I-124 | $CH_2CH_2CH_3$ | $CF_3$ |
| I-125 | F | $CF_3$ |
| I-126 | Cl | $CF_3$ |
| I-127 | Br | $CF_3$ |
| I-128 | I | $CF_3$ |
| I-129 | $SCH_3$ | $CF_3$ |
| I-130 | $SCH_2CH_3$ | $CF_3$ |
| I-131 | $CF_3$ | $CF_3$ |
| I-132 | $CF_2CF_3$ | $CF_3$ |
| I-133 | CN | $CF_3$ |
| I-134 | CHO | $CF_3$ |
| I-135 | H | C(=O)$OCH_3$ |
| I-136 | $CH_3$ | C(=O)$OCH_3$ |
| I-137 | $CH_2CH_3$ | C(=O)$OCH_3$ |
| I-138 | $CH_2CH_2CH_3$ | C(=O)$OCH_3$ |
| I-139 | F | C(=O)$OCH_3$ |
| I-140 | Cl | C(=O)$OCH_3$ |
| I-141 | Br | C(=O)$OCH_3$ |
| I-142 | I | C(=O)$OCH_3$ |
| I-143 | $SCH_3$ | C(=O)$OCH_3$ |
| I-144 | $SCH_2CH_3$ | C(=O)$OCH_3$ |
| I-145 | $CF_3$ | C(=O)$OCH_3$ |
| I-146 | $CF_2CF_3$ | C(=O)$OCH_3$ |
| I-147 | CN | C(=O)$OCH_3$ |
| I-148 | H | C(=O)$OCH_2CH_3$ |
| I-149 | $CH_3$ | C(=O)$OCH_2CH_3$ |
| I-150 | $CH_2CH_3$ | C(=O)$OCH_2CH_3$ |
| I-151 | $CH_2CH_2CH_3$ | C(=O)$OCH_2CH_3$ |
| I-152 | F | C(=O)$OCH_2CH_3$ |
| I-153 | Cl | C(=O)$OCH_2CH_3$ |
| I-154 | Br | C(=O)$OCH_2CH_3$ |
| I-155 | I | C(=O)$OCH_2CH_3$ |
| I-156 | $SCH_3$ | C(=O)$OCH_2CH_3$ |
| I-157 | $SCH_2CH_3$ | C(=O)$OCH_2CH_3$ |
| I-158 | $CF_3$ | C(=O)$OCH_2CH_3$ |
| I-159 | $CF_2CF_3$ | C(=O)$OCH_2CH_3$ |
| I-160 | CN | C(=O)$OCH_2CH_3$ |
| I-161 | H | C(=O)$OCH_2CH_2CH_3$ |
| I-162 | $CH_3$ | C(=O)$OCH_2CH_2CH_3$ |
| I-163 | $CH_2CH_3$ | C(=O)$OCH_2CH_2CH_3$ |
| I-164 | $CH_2CH_2CH_3$ | C(=O)$OCH_2CH_2CH_3$ |
| I-165 | F | C(=O)$OCH_2CH_2CH_3$ |
| I-166 | Cl | C(=O)$OCH_2CH_2CH_3$ |
| I-167 | Br | C(=O)$OCH_2CH_2CH_3$ |
| I-168 | I | C(=O)$OCH_2CH_2CH_3$ |
| I-169 | $SCH_3$ | C(=O)$OCH_2CH_2CH_3$ |
| I-170 | $SCH_2CH_3$ | C(=O)$OCH_2CH_2CH_3$ |
| I-171 | $CF_3$ | C(=O)$OCH_2CH_2CH_3$ |
| I-172 | $CF_2CF_3$ | C(=O)$OCH_2CH_2CH_3$ |
| I-173 | CN | C(=O)$OCH_2CH_2CH_3$ |
| I-174 | H | C(=O)OCH($CH_3$)$_2$ |
| I-175 | $CH_3$ | C(=O)OCH($CH_3$)$_2$ |
| I-176 | $CH_2CH_3$ | C(=O)OCH($CH_3$)$_2$ |
| I-177 | $CH_2CH_2CH_3$ | C(=O)OCH($CH_3$)$_2$ |
| I-178 | F | C(=O)OCH($CH_3$)$_2$ |
| I-179 | Cl | C(=O)OCH($CH_3$)$_2$ |
| I-180 | Br | C(=O)OCH($CH_3$)$_2$ |
| I-181 | I | C(=O)OCH($CH_3$)$_2$ |
| I-182 | $SCH_3$ | C(=O)OCH($CH_3$)$_2$ |
| I-183 | $SCH_2CH_3$ | C(=O)OCH($CH_3$)$_2$ |
| I-184 | $CF_3$ | C(=O)OCH($CH_3$)$_2$ |
| I-185 | $CF_2CF_3$ | C(=O)OCH($CH_3$)$_2$ |
| I-186 | CN | C(=O)OCH($CH_3$)$_2$ |
| I-187 | H | C(=O)$OCH_2CH_2CH_2CH_3$ |
| I-188 | $CH_3$ | C(=O)$OCH_2CH_2CH_2CH_3$ |
| I-189 | $CH_2CH_3$ | C(=O)$OCH_2CH_2CH_2CH_3$ |
| I-190 | $CH_2CH_2CH_3$ | C(=O)$OCH_2CH_2CH_2CH_3$ |
| I-191 | F | C(=O)$OCH_2CH_2CH_2CH_3$ |
| I-192 | Cl | C(=O)$OCH_2CH_2CH_2CH_3$ |
| I-193 | Br | C(=O)$OCH_2CH_2CH_2CH_3$ |
| I-194 | I | C(=O)$OCH_2CH_2CH_2CH_3$ |
| I-195 | $SCH_3$ | C(=O)$OCH_2CH_2CH_2CH_3$ |
| I-196 | $SCH_2CH_3$ | C(=O)$OCH_2CH_2CH_2CH_3$ |
| I-197 | $CF_3$ | C(=O)$OCH_2CH_2CH_2CH_3$ |
| I-198 | $CF_2CF_3$ | C(=O)$OCH_2CH_2CH_2CH_3$ |
| I-199 | CN | C(=O)$OCH_2CH_2CH_2CH_3$ |

Particular preference is given to the combinations of one of the compounds I-135, I-161 and I-187 of table 3, I-27 of table 4, I-62 of table 7 and I-22 of table 55 with one of the active compounds, defined at the outset, from groups A) to O), especially preferred is the compound I-62 of table 7, N,N-dimethyl-3-(3-bromo-6-fluoro-2-methylindole-1-sulfonyl)-[1,2,4]triazole-1-sulfonamide (compound IA).

A preferred embodiment of the invention provides mixtures of a compound I with the compound of the formula II.

A further embodiment of the invention provides mixtures of a compound I with an oxime ether derivative of the formula III.

From among the compounds of the formula III, preference is given to those in which X is a difluoromethoxy group. In addition, particular preference is given to compounds of the formula III in which the index n is zero.

Particularly preferred compounds III are especially the compounds listed in table III below:

TABLE III

| No. | X | $R_n$ |
|---|---|---|
| III-1 | $OCF_3$ | H |
| III-2 | $OCHF_2$ | H |
| III-3 | $OCH_2F$ | H |
| III-4 | $OCF_3$ | 4-$OCH_3$ |
| III-5 | $OCHF_2$ | 4-$OCH_3$ |
| III-6 | $OCH_2F$ | 4-$OCH_3$ |
| III-7 | $OCF_3$ | 4-F |
| III-8 | $OCHF_2$ | 4-F |
| III-9 | $OCH_2F$ | 4-F |
| III-10 | $OCF_3$ | 4-Cl |

TABLE III-continued

| No. | X | $R_n$ |
|---|---|---|
| III-11 | $OCHF_2$ | 4-Cl |
| III-12 | $OCH_2F$ | 4-Cl |
| III-13 | $OCF_3$ | 4-$CH_3$ |
| III-14 | $OCHF_2$ | 4-$CH_3$ |
| III-15 | $OCH_2F$ | 4-$CH_3$ |
| III-16 | $OCF_3$ | 4-$CF_3$ |
| III-17 | $OCHF_2$ | 4-$CF_3$ |
| III-18 | $OCH_2F$ | 4-$CF_3$ |
| III-19 | $OCF_3$ | 4-$CF_3$ |

The compound III-2 is especially preferred.

Another embodiment of the invention provides mixtures of a compound I with a compound of the formula IV.

Preference is given to compounds of the formula IV in which $R^{41}$ is n-propyl or n-butyl, in particular n-propyl.

In addition, particular preference is given to compounds of the formula IV in which $R^{43}$ is iodine or bromine, in particular iodine.

The formula IV represents in particular compounds of the formulae IV.1, IV.2 and IV.3:

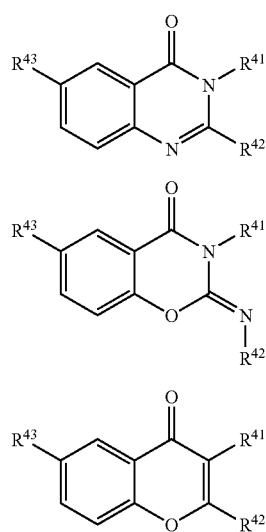

in which the variables have the meanings given for formula IV.

The compound of the formula IV.1 in which $R^{41}$ is n-propyl, $R^{42}$ is n-propoxy and $R^{43}$ is iodine is known under the common name proquinazid (compound IV.1-1). Mixtures of a compound of the formula I and proquinazid are a preferred embodiment of the invention.

In addition, mixtures comprising a compound of the formula I and a compound of the formula IV.2 are also a preferred embodiment of the invention.

Especially preferred are the mixtures with a compound I and one of the following compounds of the formula IV.2:

| No. | $R^{41}$ | $R^{42}$ | $R^{43}$ |
|---|---|---|---|
| IV.2-1 | $CH_2CH_2CH_3$ | $OCH_3$ | I |
| IV.2-2 | $CH_2CH_2CH_2CH_3$ | $OCH_2CH_3$ | I |
| IV.2-3 | $CH_2CH_2CH_3$ | $OCH_2CH_3$ | I |
| IV.2-4 | $CH_2CH_2CH_3$ | $OCH(CH_3)_2$ | I |

A further preferred embodiment of the invention relates to mixtures of a compound I and one of the following compounds of the formula IV.3:

| No. | $R^{41}$ | $R^{42}$ | $R^{43}$ |
|---|---|---|---|
| IV.3-1 | $CH_2CH_2CH_3$ | $OCH_3$ | I |
| IV.3-2 | $CH_2CH_2CH_2CH_3$ | $OCH_2CH_3$ | I |
| IV.3-3 | $CH_2CH_2CH_3$ | $OCH_2CH_3$ | I |
| IV.3-4 | $CH_2CH_2CH_3$ | $OCH(CH_3)_2$ | I |
| IV.3-5 | $CH_2CH_2CH_3$ | $OCH_2CH_2CH_3$ | I |
| IV.3-6 | $CH_2CH_2CH_3$ | $OCH_2CH_2CH_2CH_3$ | I |
| IV.3-7 | $CH_2CH_2CH_3$ | $OCH_3$ | Br |
| IV.3-8 | $CH_2CH_2CH_2CH_3$ | $OCH_2CH_3$ | Br |
| IV.3-9 | $CH_2CH_2CH_3$ | $OCH_2CH_3$ | Br |
| IV.3-10 | $CH_2CH_2CH_3$ | $OCH(CH_3)_2$ | Br |
| IV.3-11 | $CH_2CH_2CH_3$ | $OCH_2CH_2CH_3$ | Br |
| IV.3-12 | $CH_2CH_2CH_3$ | $OCH_2CH_2CH_2CH_3$ | Br |

Here, particular preference is given to mixtures of a compound I with compounds IV.3-6 or IV.3-12, especially IV.3-6.

A further preferred embodiment of the mixtures according to the invention relates to the combination of one of the abovementioned compounds of the formula I and strobilurins, such as azoxystrobin, fluoxastrobin, picoxystrobin, pyraclostrobin or trifloxystrobin.

A further preferred embodiment of the mixtures according to the invention relates to the combination of one of the abovementioned compounds of the formula I and acylalanines, such as benalaxyl, metalaxyl, mefenoxam, ofurace or oxadixyl.

A further preferred embodiment of the mixtures according to the invention relates to the combination of one of the abovementioned compounds of the formula I and cinnamides and analogs, such as dimethomorph, flumetover or flumorph.

A further preferred embodiment of the mixtures according to the invention relates to the combination of one of the abovementioned compounds of the formula I and heterocyclic compounds, such as dithianon, picobenzamid, thiophanate-methyl or triforine.

A further preferred embodiment of the mixtures according to the invention relates to the combination of one of the abovementioned compounds of the formula I and sulfur or copper fungicides, such as Bordeaux mixture, copper acetate, copper oxychloride, basic copper sulfate.

A further preferred embodiment of the mixtures according to the invention relates to the combination of one of the abovementioned compounds of the formula I and an active compound from the group consisting of captafol, dichlofluanid, tolylfluanid, benthiavalicarb, chlorothalonil, cyflufenamid, diclofluanid, diethofencarb, ethaboxam, fenhexamid, fluazinam, iprovalicarb, metrafenone and zoxamide.

When preparing the mixtures, it is preferred to employ the pure active compounds I and II, to which further active compounds against harmful fungi or against other pests, such as insects, arachnids or nematodes, or else herbicidal or growth-regulating active compounds or fertilizers can be added as further active components according to need.

Usually, mixtures of the compound I with an active compound from groups A) to O) are employed. However, in certain cases mixtures of the compound I with two or, if appropriate, more active components may be advantageous.

Suitable further active components in the above sense are in particular the active compounds, mentioned at the outset, from groups A) to O) and in particular the preferred active compounds mentioned above.

The compound I and the active compound from groups A) to O) are usually applied in a weight ratio of from 100:1 to 1:100, preferably from 20:1 to 1:20, in particular from 10:1 to 1:10.

The further active components are, if desired, added in a ratio of from 20:1 to 1:20 to the compound I.

Depending on the type of compound and the desired effect, the application rates of the mixtures according to the invention are from 5 g/ha to 2000 g/ha, preferably from 50 to 900 g/ha, in particular from 50 to 750 g/ha.

Correspondingly, the application rates for the compound I are generally from 1 to 1000 g/ha, preferably from 10 to 900 g/ha, in particular from 20 to 750 g/ha.

Correspondingly, the application rates for the active compound from groups A) to O) are generally from 1 to 2000 g/ha, preferably from 10 to 900 g/ha, in particular from 40 to 500 g/ha.

In the treatment of seed, application rates of mixture are generally from 1 to 1000 g/100 kg of seed, preferably from 1 to 750 g/100 kg, in particular from 5 to 500 g/100 kg.

The method for controlling harmful fungi is carried out by the separate or joint application of the compound I and the active compound from groups A) to O) or the mixtures of the compound I and the active compound from groups A) to O) by spraying or dusting the seeds, the plants or the soil before or after sowing of the plants or before or after emergence of the plants.

The mixtures according to the invention, or the compound I and the active compound from groups A) to O), can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations: 1. Products for dilution with water

A) Water-Soluble Concentrates (SL)

10 parts by weight of the active compounds are dissolved in water or in a water-soluble solvent. As an alternative, wetters or other auxiliaries are added. The active compound dissolves upon dilution with water.

B) Dispersible Concentrates (DC)

20 parts by weight of the active compounds are dissolved in cyclohexanone with addition of a dispersant, for example polyvinylpyrrolidone. Dilution with water gives a dispersion.

C) Emulsifiable Concentrates (EC)

15 parts by weight of the active compounds are dissolved in xylene with addition of calcium dodecylbenzenesulfonate and castor oil ethoxylate (in each case 5% strength). Dilution with water gives an emulsion.

D) Emulsions (EW, EO)

40 parts by weight of the active compounds are dissolved in xylene with addition of calcium dodecylbenzenesulfonate and castor oil ethoxylate (in each case 5% strength). This mixture is introduced into water by means of an emulsifying machine (Ultraturrax) and made into a homogeneous emulsion. Dilution with water gives an emulsion.

E) Suspensions (SC, OD)

In an agitated ball mill, 20 parts by weight of the active compounds are comminuted with addition of dispersants, wetters and water or an organic solvent to give a fine active compound suspension. Dilution with water gives a stable suspension of the active compound.

F) Water-Dispersible Granules and Water-Soluble Granules (WG, SG)

50 parts by weight of the active compounds are ground finely with addition of dispersants and wetters and prepared as water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)

75 parts by weight of the active compounds are ground in a rotor-stator mill with addition of dispersants, wetters and silica gel. Dilution with water gives a stable dispersion or solution of the active compound.

2. Products to be Applied Undiluted

H) Dustable Powders (DP)

5 parts by weight of the active compounds are ground finely and mixed intimately with 95% of finely divided kaolin. This gives a dustable product.

I) Granules (GR, FG, GG, MG)

0.5 part by weight of the active compounds is ground finely and associated with 95.5% carriers. Current methods are extrusion, spray-drying or the fluidized bed. This gives granules to be applied undiluted.

J) ULV Solutions (UL)

10 parts by weight of the active compounds are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Oils of various types, wetters, adjuvants, herbicides, fungicides, other pesticides, or bactericides may be added to the active compounds, even, if appropriate, not until immediately prior to use (tank mix). These agents are typically admixed with the compositions according to the invention in a weight ratio of from 1:10 to 10:1.

The compounds I and A) to O) or the mixtures or the corresponding formulations are applied by treating the harmful fungi, the plants, seeds, soils, areas, materials or spaces to be kept free from them with a fungicidally effective amount of the mixture or, in the case of separate application, of the compounds I and A) to O). Application can be carried out before or after infection by the harmful fungi.

The fungicidal effect of the compound and the mixtures can be demonstrated by the following tests:

The active compounds, separately or jointly, were prepared as a stock solution comprising 0.25% by weight of active compound in acetone or DMSO. 1% by weight of the emulsifier Uniperol® EL (wetting agent having emulsifying and dispersant action based on ethoxylated alkylphenols) was added to this solution, and the mixture was diluted with water to the desired concentration.

The visually determined percentages of infected leaf areas were converted into efficacies in % of the untreated control:

The efficacy (E) is calculated as follows using Abbot's formula:

$$E=(1-\alpha/\beta)\cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of mixtures of active compounds were determined using Colby's formula (Colby, S. R. "Calculating synergistic and antagonistic responses of herbicide Combinations", Weeds, 15, 20-22, 1967) and compared with the observed efficacies.

Colby's formula:

$$E=x+y-x\cdot y/100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b

USE EXAMPLE 1

Activity Against Late Blight on Tomatoes Caused by *Phytophthora infestans*, Protective Application Leaves of potted tomato plants were sprayed to runoff point with an aqueous suspension having the concentration of active compound given below. The next day, the leaves were infected with an aqueous sporangia suspension of *Phytophthora infestans*. The plants were then placed in a water-vapor-saturated chamber at temperatures between 18 and 20° C. After 6 days, the blight on the untreated but infected control plants had developed to such an extent that the infection could be determined visually in %.

TABLE A

| | individual active compounds | | |
|---|---|---|---|
| Example | Active compound/ mixing ratio | Concentration of active compound in the spray liquor [ppm] | Efficacy in % of the untreated control |
| 1 | control (untreated) | — | (90% infection) |
| 2 | I-62, Tab.7 (IA) | 1 | 56 |
| 3 | II | 4 | 0 |
| | | 1 | 0 |
| | | 0.25 | 0 |

TABLE B

| | mixtures according to the invention | | |
| --- | --- | --- | --- |
| Example | Active compound mixture Concentration Mixing ratio | Observed efficacy | Calculated efficacy*) |
| 4 | IA + II<br>1 + 4 ppm<br>1:4 | 89 | 56 |
| 5 | IA + II<br>1 + 1 ppm<br>1:1 | 78 | 56 |
| 6 | IA + II<br>1 + 0.25 ppm<br>4:1 | 67 | 56 |

*)efficacy calculated using Colby's formula

The test results show that, by virtue of strong synergism, the activity of the mixtures according to the invention is considerably higher than had been predicted using Colby's formula.

We claim:

1. A fungicidal mixture comprising, as active components,
1) N,N-dimethyl-3-(3-bromo-6-fluoro-2-methylindole-1-sulfonyl)-[1,2,4]triazole-1-sulfonamide of the formula IA

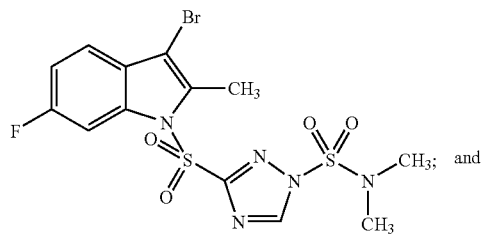

2) at least one active compound selected from the following groups:
A) strobilurins: azoxystrobin, dimoxystrobin, enestroburin, fluoxastrobin, kresoxim-methyl, metominostrobin, orysastrobin, picoxystrobin, pyraclostrobin or trifloxystrobin;
B) acylalanines: benalaxyl, metalaxyl, mefenoxam, ofurace, oxadixyl;
C) cinnamides: dimethomorph, flumetover or flumorph; and
D) 5-chloro-7-(4-methylpiperidin-1-yl)-6-(2,4,6-trifluorophenyl)-[1,2,4]triazolo[1,5-a]pyrimidine of the formula II,

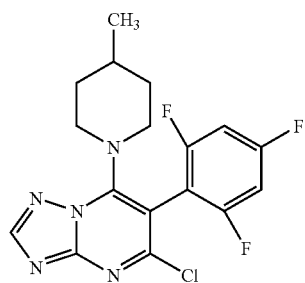

in a synergistically effective amount.

2. The fungicidal mixture according to claim 1, comprising the compound of formula IA and azoxystrobin, fluoxastrobin, picoxystrobin, pyraclostrobin or trifloxystrobin.
3. The fungicidal mixture according to claim 1, comprising the compound of formula IA and benalaxyl, metalaxyl, mefenoxam, ofurace or oxadixyl.
4. The fungicidal mixture according to claim 1, comprising the compound of formula IA and dimethomorph, flumetover or flumorph.
5. The fungicidal mixture according to claim 1, comprising the compound of formula IA and the compound of the formula II.
6. The fungicidal mixture according to claim 5, comprising a further active compound from groups A) to D) or from groups E) to P):
E) azoles selected from the group consisting of cyproconazole, difenoconazole, enilconazole, epoxiconazole, fluquinconazole, flusilazole, hexaconazole, imazalil, metconazole, myclobutanil, penconazole, prochloraz, prothioconazole, tebuconazole, triadimefon, triadimenol, and triflumizole;
F) spiroxamine;
G) anilinopyrimidines selected from the group consisting of pyrimethanil, mepanipyrim and cyprodinil;
H) dicarboximides selected from the group consisting of iprodione, procymidone, and vinclozolin;
I) dithiocarbamates selected from the group consisting of ferbam, nabam, maneb, metam, metiram, propineb, polycarbamate, thiram, ziram and zineb;
K) heterocyclic compounds selected from the group consisting of benomyl, boscalid, carbendazim, dithianon, famoxadone, fenamidone, penthiopyrad, picobenzamid, proquinazid, quinoxyfen, thiophanate-methyl, and triforine,
L) sulfur and copper fungicides selected from the group consisting of Bordeaux mixture, copper acetate, copper oxychloride, and basic copper sulfate;
M) dinocap;
N) phenylpyrroles selected from the group consisting of fenpiclonil and fludioxonil;
O) sulfenic acid derivatives selected from the group consisting of captafol, dichlofluanid, and tolylfluanid;
P) other fungicides selected from the group consisting of benthiavalicarb, chlorothalonil, cyflufenamid, dicloflu-anid, diethofencarb, ethaboxam, fenhexamid, fluazinam, iprovalicarb, mandipropamid, metrafenone, zoxamide;
oxime ether derivatives of the formula III,

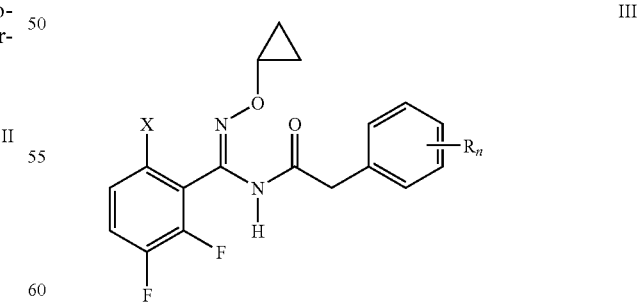

in which
X is $C_1$-$C_4$-haloalkoxy,
n is 0, 1, 2 or 3,
R is halogen, $C_1$-$C_4$-alkyl, $C_1$-$C_4$-haloalkyl, $C_1$-$C_4$-alkoxy or haloalkoxy; and compounds of the formula IV,

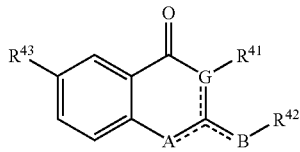

in which the variables are as defined below:
A is O or N;
B is N or a direct bond;
G is C or N;
$R^{41}$ is $C_1$-$C_4$-alkyl;
$R^{42}$ is $C_1$-$C_4$-alkoxy; and
$R^{43}$ is halogen.

7. The fungicidal mixture according to claim 1, comprising a compound of the formula I and an active compound from groups A) to D) in a weight ratio of from 4:1 to 1:4.

8. A composition, comprising a solid or liquid carrier and a mixture according to claim 1.

9. A method for controlling harmful fungi, wherein the fungi, their habitat or the plants, the soil or seed to be protected against fungal attack are/is treated with a synergistically effective amount of a compound of formula IA and an active compound from groups A) to D) according to claim 1.

10. The method according to claim 9, wherein the compound of formula IA and the active compound from groups A) to D) are applied simultaneously, that is jointly or separately, or in succession.

11. The method according to claim 9, wherein the compound of formula IA and an active compound from groups A) to D) are applied to the soil or the plants to be protected against fungal attack in an amount of from 5 g/ha to 2000 g/ha.

12. The method according to claim 9, wherein the compound of formula IA and an active compound from groups A) to D) are applied in an amount of from 1 to 1000 g/100 kg of seed.

13. The method according to claim 9, wherein harmful fungi from the class of the Oomycetes are controlled.

14. The fungicidal mixture according to claim 1, comprising the compound of the formula IA and azoxystrobin.

15. The fungicidal mixture according to claim 1, comprising the compound of the formula IA and pyraclostrobin.

16. The fungicidal mixture according to claim 1, comprising the compound of the formula IA and metalaxyl.

17. The fungicidal mixture according to claim 1, comprising the compound of the formula IA and dimethomorph.

18. The fungicidal mixture according to claim 14, comprising compound IA and azoxystrobin in a weight ratio of 1:4 to 4:1.

19. The fungicidal mixture according to claim 15, comprising compound IA and pyraclostrobin in a weight ratio of 1:4 to 4:1.

20. The fungicidal mixture according to claim 16, comprising compound IA and metalaxyl in a weight ratio of 1:4 to 4:1.

21. The fungicidal mixture according to claim 17, comprising compound IA and dimethomorph in a weight ratio of 1:4 to 4:1.

* * * * *